United States Patent
Motzer et al.

(10) Patent No.: US 8,249,832 B2
(45) Date of Patent: Aug. 21, 2012

(54) CORRELATION OF INSPECTION INFORMATION AND COMPUTER-AIDED DESIGN DATA FOR STRUCTURAL ASSESSMENT

(75) Inventors: William P. Motzer, Seattle, WA (US); Gary Georgeson, Federal Way, WA (US); Scott W. Lea, Renton, WA (US); Dennis Coffey, Woodinville, WA (US)

(73) Assignee: The Boeing Company, Chicago, IL (US)

( * ) Notice: Subject to any disclaimer, the term of this patent is extended or adjusted under 35 U.S.C. 154(b) by 328 days.

(21) Appl. No.: 12/631,810

(22) Filed: Dec. 5, 2009

(65) Prior Publication Data

US 2011/0137615 A1    Jun. 9, 2011

(51) Int. Cl.
*G06F 15/00* (2006.01)
*G06F 17/50* (2006.01)
*G06K 9/00* (2006.01)

(52) U.S. Cl. .............................. 702/189; 703/1; 382/144

(58) Field of Classification Search .................. 702/189; 235/375; 703/1; 382/144, 145
See application file for complete search history.

(56) References Cited

U.S. PATENT DOCUMENTS

| 6,766,282 B1 * | 7/2004 | Schettine ........................... 703/1 |
| 6,865,288 B1 * | 3/2005 | Shishido et al. .............. 382/145 |
| 7,664,308 B2 * | 2/2010 | Isomura ........................ 382/144 |
| 2007/0000991 A1 | 1/2007 | Matsen et al. ................ 235/375 |
| 2009/0287427 A1 | 11/2009 | DuBois |

OTHER PUBLICATIONS

International Search Report mailed Mar. 11, 2011.
Turner, W. et al., Using Computer Vison to Map Laser Ultrasound onto CAD Geometries, AIP Conference Proceedings, American Institute of Physics, New York, US, vol. 22, No. 657A, Jan. 1, 2003.

\* cited by examiner

*Primary Examiner* — Bryan Bui
(74) *Attorney, Agent, or Firm* — Caven & Aghevli LLC

(57) ABSTRACT

A system and method for correlating data is provided. Generally, the system contains a scanning system having at least one inspection emitter. The scanning system situated to scan a structure and produce a quantity of inspection information. A local positioning system is in communication with the scanning system and situated to detect a location of the quantity of inspection information in relation to the structure. A quantity of computer-aided design data corresponding to the quantity of inspection information is included. An imaging system is in communication with the scanning system and the local positioning system, the imaging system situated to produce an overlay image of at least two of an image based from the structure, an image based from the quantity of inspection information and an image formed from at least a portion of the quantity of computer-aided design data.

18 Claims, 4 Drawing Sheets

CORRELATION OF INSPECTION INFORMATION AND COMPUTER-AIDED DESIGN DATA FOR STRUCTURAL ASSESSMENT

FIELD OF THE DISCLOSURE

The present disclosure is generally related to data correlation and more particularly is related to the correlation of inspection information and computer-aided design data for structural assessment. The disclosure has particular utility when used in connection with non-destructive inspection of aircraft structures during construction and repair, and will be described in connection with such utilities, although other utilities are contemplated.

BACKGROUND OF THE DISCLOSURE

When repair work is required on structures, such as vehicles or the skin of an aircraft, for example, it may be necessary to take into account the size, shape and location of previous damage and/or repairs for optimum repair of the structure. Photographs of the previous damage and/or repair may be made but may not be precisely located or sized on the structure or may not be useful for future repair planning. During the analysis of a damage/repair site (i.e. a location of interest) it may be desirable to obtain measurement information without contacting the structure. Due to accessibility and/or contact constraints, it may be difficult to reach the location of interest to obtain position measurements.

Local positioning systems which have been used to determine the location, shape and size of damage and/or repairs on structures, such as skin damage and/or repairs on an aircraft, for example, may utilize acoustic, laser-based, magnetic, RFID, GPS, and motion capture-based systems. A local positioning system may utilize a minimum of four wireless acoustic sensors (and may require line-of-site) to provide 3-D positioning capability of past damage and/or repairs. The sensors may require mounting on the structure with the fourth sensor used to generate point data. Also, curvature of any sort on the surface of the structure distorts the acoustic path and reduces the precision to the point that this method will not work in many cases.

Laser-based positioning systems may stand off the structure to take location data on a structure. Other laser-based systems require receivers or reflectors placed at locations of interest. Multiple laser emitters may need to be placed around the work volume, which increases process complexity and data collection effort of the user. In a similar manner, motion capture (MoCap) systems may also require the placement of components around the work volume, in this case multiple camera units, and also require the placement of markers on the target object. Other systems also have shortcomings as well, such as magnetic systems that which require placement of magnetic sensors and tend to have accuracy problems due to interference from any metal on a structure. Global Positioning Systems and active RFID-based systems don't have the necessary resolution, and also require device placement on the target object.

Thus, a heretofore unaddressed need exists in the industry to address the aforementioned deficiencies and inadequacies.

SUMMARY OF THE DISCLOSURE

Embodiments of the present disclosure provide a system and method for the correlation of inspection information and computer-aided design data for structural assessment. Briefly described, in architecture, one embodiment of the system, among others, can be implemented as follows. The data correlation system contains a scanning system having at least one inspection emitter. The scanning system is situated to scan a portion of a structure and produce a quantity of inspection information. A local positioning system is in communication with the scanning system and situated to detect a location of the portion structure in relation to the structure. A quantity of computer-aided design data corresponds to the quantity of inspection information. An imaging system is in communication with the scanning system and the local positioning system. The imaging system is situated to produce an overlay image of at least two of an image based from the portion of the structure, an image based from the quantity of inspection information and an image formed from at least a portion of the quantity of computer-aided design data.

The present disclosure can also be viewed as providing methods of correlating data for improved structural assessment. In this regard, one embodiment of such a method, among others, can be broadly summarized by the following steps: initiating an inspection scan to produce a quantity of inspection information; locating a first position of the inspection scan with a local positioning system; transferring a first coordinate corresponding to the measured first position to an inspection system; overlaying a quantity of computer-aided design data on the quantity of inspection information in an imaging system.

The present disclosure can also be viewed as a computer readable medium encoded with computer readable program code, the computer readable program code having instructions. In this regard, the computer readable program code may: initiate an inspection scan to produce a quantity of non-destructive inspection information corresponding to a structure; mark a start position and a stop position of the inspection scan; measure the start position and the stop position of the inspection scan with a local positioning system, wherein the local positioning system is in communication with a coordinate system; transfer a quantity of coordinate information, wherein the coordinate information corresponds to the measured start position and stop position to an inspection system; select a quantity of computer-aided design data from a database, wherein at least a portion of the quantity of computer-aided design data corresponds to the inspection scan; and overlay the quantity of computer-aided design data on the quantity of non-destructive inspection information in an imaging system.

The features, functions, and advantages that have been discussed can be achieved independently in various embodiments of the present disclosure or may be combined in yet other embodiments further details of which can be seen with reference to the following description and drawings.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
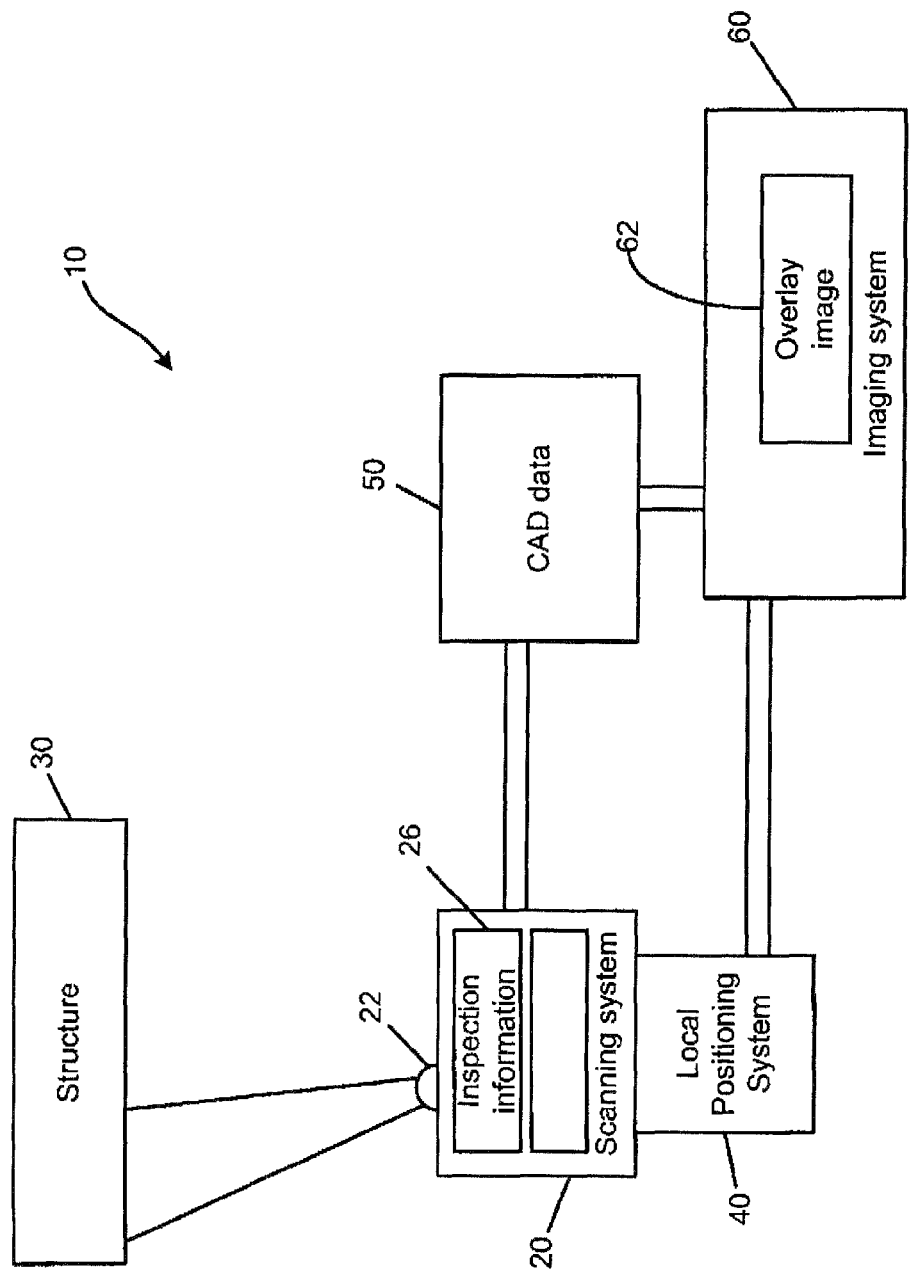
FIG. 1 is an illustration of a data correlation system, in accordance with a first exemplary embodiment of the present disclosure.

FIG. 1 is an illustration of a data correlation system 10, in accordance with a first exemplary embodiment of the present disclosure. The data correlation system 10 includes a scanning system 20 having at least one inspection emitter 22. The scanning system 20 is situated to scan a structure 30 and produce a quantity of inspection information 26. A local positioning system (LPS) 40, is in communication with the scanning system 20 and situated to detect a location of the quantity of inspection information 26 in relation to the structure 30. A quantity of computer-aided design (CAD) data 50 corresponding to the quantity of inspection information 26 is included. An imaging system 60 is in communication with the scanning system 20 and the local positioning system 40. The imaging system 60 is situated to produce an overlay image 62 of at least two of an image based from the structure 30, an image based from the quantity of inspection information 26 and an image formed from at least a portion of the quantity of CAD data 50.

The scanning system 20 of the data correlation system 10 may include a variety of configurations and scanning techniques. The scanning system 20 may be any scanning technique known to those having ordinary skill in the art. Generally, this may include one of a non-destructive scanning technique, which may also be referred to as non-destructive inspection (NDI), and a non-NDI scanning technique. Both an NDI scanning technique and a non-NDI scanning technique, or any combination thereof, may be used with the scanning system 20 to provide successful results with the data correlation system 10.

A NDI scanning technique may be considered any technique, method or process, or combination thereof that is used to evaluate the properties of a structure without causing permanent damage to that structure. Types of non-destructive scanning techniques may include ultrasonic, thermographic, magnetic-particle, liquid penetrant and radiographic, among others. All types of non-destructive scanning techniques are considered within the scope of the present disclosure. A NDI scanning technique may prove to be the most desirable scanning technique in the scanning system 20 because it will not permanently damage the structure 30 that is scanned. However, non-NDI scanning techniques may also be used successfully in the scanning system 20. Generally, non-NDI scanning techniques include all scanning techniques that do not qualify as NDI scanning techniques. The damage caused to a structure 30 with non-NDI scanning techniques may vary greatly and will largely depend on the type of technique and the frequency that the technique is used. For example, one type of non-NDI scanning technique may cause damage to the structure 30 after only one use, whereas another type of non-NDI scanning technique may cause damage only after a large number of uses.

Additionally, although a non-NDI scanning technique may cause damage to the structure 30, it may only cause very minimal damage, such as, for example, a discoloration or other cosmetic damage. Very minimal damage to the structure 30 may not inhibit the utility or integrity of the structure 30 being scanned. Therefore, a non-NDI scanning technique that causes very little damage may be employed in the scanning system 20. Likewise, a non-NDI scanning technique that or only causes damage after a large number of uses may also be employed in the scanning system 20, since damage to the structure 30 can be prevented by limiting the number of uses of the scanning technique. Any potential damage due to any scanning technique may be limited by the scanning system 20 or another component of the data correlation system 10, such that the technique is only used to the extent that the structure is subjected to only de minimis damage.

The scanning system 20 includes at least one inspection emitter 22, but may more commonly include a plurality of inspection emitters 22. The inspection emitter 22 may be any device that is used to gather information by exuding a material, substance or energy. This may include, but is not limited to a device that exudes a quantity of energy, a signal, a wave, a light beam or another energy. The inspection emitter 22 may be compatible with the type of scanning technique used within the scanning system 20. For example, if an ultrasonic scanning technique is used, an ultrasonic inspection emitter should be used. The inspection emitter 22 may include a variety of emitters, such as an ultrasonic emitter, a thermographic emitter, a radiographic emitter or a magnetic-particle emitter, depending on the type of scanning system 20 used. Additionally, inspection emitters 22 may be compatible with any scanning technique or scanning system 20. Inspection emitters may also be configured to be compatible with more than one scanning system 20, to provide for concurrent use of an inspection emitter 22, interchangeability of parts or for use with a wide range of scanning systems 20.

The inspection emitter 22 may be included in the scanning system 20 in a variety of configurations. For example, the inspection emitter 22 may be an integral component with the scanning system 20 or it may be in communication with the scanning system 20. Additionally, any other variation on the design and communication of the inspection emitter 22 and the scanning system 20 may be employed. This may include arrangements where the inspection emitter 22 is located remotely to the scanning system 20 and in communication with the scanning system via a wireless network or similar communication system. Additional arrangements are possible and are considered within the scope of the present disclosure.

The scanning system 20 may scan the structure 30 in accordance with a variety of configurations and designs. Some of these configurations and designs may include scanning the structure 30 only once, scanning the structure 30 a plurality of times, scanning the structure 30 according to an algorithm and commencing a scan at predetermined intervals or upon command, either automated or manual. Other design or configuration options also may be included within the scanning system 20, and may relate to any aspect of the scanning system 20, including the type of scan, the scope of the scan, the time of the scan or a resulting outcome of the scan.

The scanning system 20 is situated to produce a quantity of inspection information 26. The quantity of inspection information 26 may be any information that is produced as a result of the scan and generally may correspond to the scanning technique used and/or the type of inspection emitter 22 employed. The inspection information 26 may be produced in a variety of formats, including but not limited to, mathematical information, predetermined descriptive information, electronic data, non-electronic data, coordinate identification data, computerized data or computer-readable data. In FIG. 1, the inspection information 26 is depicted as three units of inspection information 26, but the data correlation system 10 may include any quantity of inspection information 26. Additionally, inspection information 26 may be produced in more than one format.

The structure 30 may include any natural or man-made object that is capable of being scanned. The structure 30 may include all varieties of objections, including those that are large, small, affixed or disposed on a ground surface, flying in an atmosphere, orbiting about a gravity-emitting body, etc. Preferably, the structure 30 may include an object having a purpose where it is desirable to scan or inspect a design or composition of the object. The structure 30 may include an object where inspection is difficult, because of the location of the structure 30 in relation to the scanning system 20 or because of a multi-layered composition. For example, an airplane is a structure 30 that may require scanning and inspection to assess structural integrity, but may be located a far distance from a scanning system 20 or has a layered composition that makes a purely visual inspection impractical. The structure 30 may be situated to provide relational-location information, such that the inspection information 26 may be produced in relation to the structure 30.

The local positioning system (LPS) 40 is in communication with the scanning to system 20 via a communication connection, which may include any communication connection such as a wireless network, a wired connection or an integral communication connection. In FIG. 1, the communication connection is depicted as an integral connection between the LPS 40 and the scanning system 20. The LPS 40 is situated to detect a location of the portion of the structure 30 that corresponds to the quantity of inspection information 26 produced from the scan. The LPS 40 may detect the location of an entire portion of the structure 30, or any portion of the structure 30. The location detected may be location of the portion of the structure in relation to the structure within a desired 2 degree of accuracy, e.g., a 2% degree of accuracy or within any other degree of accuracy. A degree of accuracy may be considered the closeness of a measurement of the location detected to the actual or true value of the location. The location detected may also correspond to a plurality of correlating points or an area defined by points on the structure 30. For example, the location detected may include a plurality of points that define a circumference or perimeter shape on the structure 30 corresponding to the inspection information 26.

In detecting the location of the inspection information 26, the LPS 40 may use a variety of location-identifying systems, such as a coordinate system or a directional system, which identify the location in relation to the structure 30. For example, if a coordinate system is used with the LPS 40, the detected location may be understood in terms of a three dimensional coordinate system. Additionally, quadrants or defined segments of the structure 30 may be used in detecting the location of the inspection information 26.

The quantity of CAD data 50 is included in the data correlation system 10 and corresponds to the quantity of inspection information 26 that is produced. The quantity of CAD data 50 may be understood as data that is produced through computerized technology and relates to the design, materials, manufacturing, dimensions, tolerances of the structure 30 or any other properties of the structure 30. In other words, the CAD data 50 may be an electronic representation of a three-dimensional image. Preferably, the CAD data 50 will be in the form of a computerized file, such as a file that is generated within a computer-aided design program. However, non-computerized CAD data 50 may also be used. The CAD data 50 corresponds to at least a portion of the quantity of inspection information 26.

An elementary example may be used to provide clarity in understanding how the CAD data 50 corresponds to the inspection information 26: If a given structure 30 is three-dimensional sphere having an outer surface, then the inspection information 26 may be a plurality of points that define one hemisphere of sphere. Accordingly, the CAD data 50 may be a computerized, three-dimensional depiction of the one hemisphere. Thus, the CAD data 50 corresponds to the locations of the inspection information 26 since both the CAD data 50 and the inspection information 26 are associated with one hemisphere of the three-dimensional sphere. Although this is a simplified and elementary example, the correspondence between the CAD data 50 and the inspection information 26 may be used with sophisticated and non-elementary situations. For example, the inspection information 26 may be produced from scanning an airplane, or more particularly, the skin of an airplane. The inspection information 26 may be information relating to the properties of the airplane structure or airplane skin, such as the materials or dimensions. Additionally, the inspection information 26 may provide data that relates to damage to the airplane structure or airplane skin, such as material fatigue, missing parts, deformed structure, structural cracks or heat spots.

The imaging system 60 is included in the data correlation system 10 and is in communication with the scanning system 20 and the LPS 40. Communication between the imaging system 60, the scanning system 20 and the LPS 40 may be a direct communication link, a wireless communication connection or an integral communication connection. Additionally, communication may include a direct communication connection or an indirect communication connection, such as what is depicted in FIG. 1, where the imaging system 60 is in communication with the scanning system 20 through the LPS 40. The imaging system 60 may also be in communication with any other components of the data correlation system 10, such as the CAD data 50. The imaging system 60 may be located locally or remotely with respect to any of the other systems in the data correlation system 10.

The imaging system 60 is situated to produce an overlay image 62 of at least two of the other components in the data correlation system 10. The overlay image 62 may be generally understood as an image that includes at least two images or depictions disposed on parallel planes. However, it may be common for the two images or depictions to be disposed on the same plane. Generally, the two or more images will also be aligned in a direction that is substantially perpendicular to the plane or planes on which the images are disposed, such that features of one image match-up or correspond to features of the other image. The overlay image 62 of the data correlation system 10 may be produced from overlaying at least two of an image based from the structure 30, an image based from the inspection information 26, an image formed from the CAD data 50 or any other component, structure or image that is included with or in communication with the data correlation system 10.

In most uses of the data correlation system 10, the overlay image 62 will be a two-dimensional image that is displayed on a display device. However, the overlay image 62 may also include other configurations, such as a three-dimensional image displayed on a display device or an illustration of a three-dimensional image displayed on a display device. The display device may include any known display device that is used for presenting information for visual or tactile reception. This may include, but is not limited to, an electronic display, a graphical display, a computerized display, a three-dimensional displaying system, a non-electronic graphical display system, an electro-magnetic display system, a carbon-based display system, a laser display system, a nanocrystal display system or any other display system.

In use, the overlay image 62 may assist a technician with determining any differences between the two or more images that are included in the overlay image 62, which may ultimately prove to be beneficial in assessing the structure 30. Assessments to the structure 30 may be directed towards structural assessments, damage assessments, or other assessments of the structure that may be useful in analyzing the structure 30 in an engineering capacity. Determining any differences between the two or more images may be especially beneficial when there is a variance in time between the two or more images included in the overlay image 62. For example, if the overlay image 62 is produced from an image based from the inspection information 26 and an image based from the CAD data 50, the CAD data 50 is likely to represent an original state of the structure 30 whereas the inspection information 26 may represent the structure after a number of uses or a period of time. Accordingly, the inspection information 26 may be indicative of a structure 30 that has been subjected to wear and tear or damage. When the overlay image 62 is viewed, any differences between the image based from the inspection information 26 and the image based from the CAD data 50 may correspond to the wear and tear or damage that the structure 30 has endured. The imaging system 60 may also include other systems to simplify the overlay image 62 or otherwise assist a technician with visual analysis of the overlay image 62.

Figure 2:
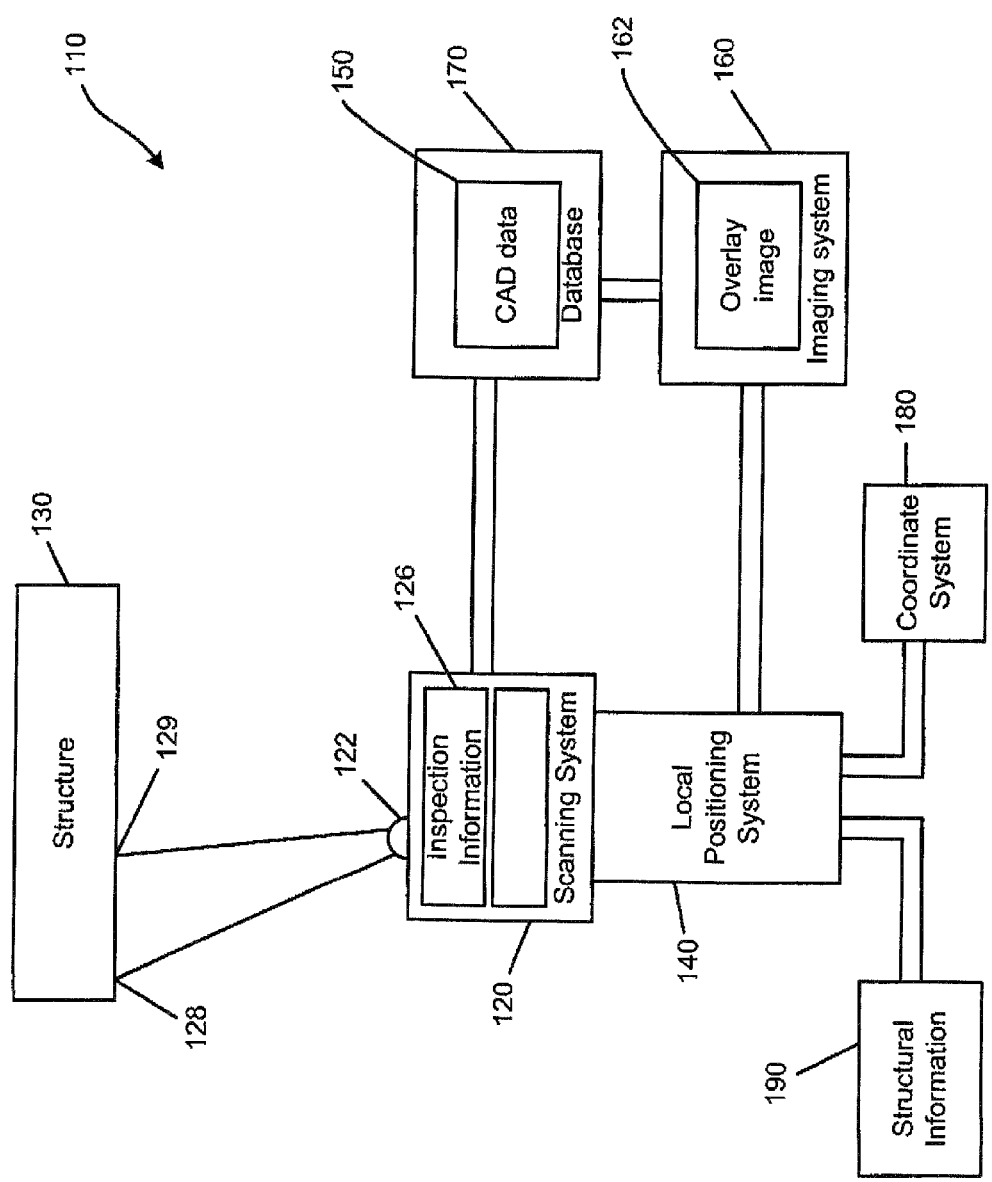
FIG. 2 is an illustration of a data correlation system, in accordance with a second exemplary embodiment of the present disclosure.

FIG. 2 is an illustration of a data correlation system 110, in accordance with a second exemplary embodiment of the present disclosure. The data correlation system 110 includes a scanning system 120 having at least one inspection emitter 122. The scanning system 120 is situated to scan a structure 130 and produce a quantity of inspection information 126. A local positioning system (LPS) 140 is in communication with the scanning system 120 and situated to detect a location of the quantity of inspection information 126 in relation to the structure 130. A quantity of computer-aided design (CAD) data 150 corresponding to the quantity of inspection information 126 is included. An imaging system 160 is in communication with the scanning system 120 and the LPS 140. The imaging system 160 is situated to produce an overlay image 162 of at least two of an image based from structure 130, an image based from the quantity of inspection information 126 and an image formed from at least a portion of the quantity of computer-aided design data 150.

The data correlation system 110 of the second exemplary embodiment may be similar to the data correlation system 10 of the first exemplary embodiment, but may include additional features and components. The inspection information 126 may include at least one scan start position 128 or scan stop position 129, or a combination thereof. The inspection information may also include a scan position with an orientation of the scan position. The scan start position 128 and the scan stop position 129 may correspond to a position where a scan is initiated or ended, respectively, an orientation of the scan or a combination thereof. A plurality of scan start positions 128 or scan stop positions 129 may be included, and a variety of arrangements or configurations may be employed. For example, the inspection information 126 may include a plurality of scan start positions 128 and scan start positions 129 that are patterned to yield inspection information 126 arranged in pulses.

The data correlation system 110 may include a variety of scanning systems 120. These may include non-destructive inspection (NDI) techniques or non-NDI techniques. Some common types of NDI scanning techniques may include ultrasonic-based, thermographic, magnetic-particle, liquid penetrant, radiographic and eddy-current testing, among others. All types of non-destructive scanning techniques are considered within the scope of the present disclosure. The inspection information 126 that is produced in the data correlation system 110 may include NDI or non-NDI inspection information 126, or a combination thereof. At least a portion of the inspection information 126 may correspond to a scan starting point, regardless of whether it is based on an NID or non-NDI inspection technique.

The structure 130 may include any natural or man-made object that is capable of being scanned. The structure 130 may include all varieties of objects, including those that are large, small, affixed or disposed on a ground surface or any other object that may require scanning in parts. The LPS 140 may be situated to detect an exact location of the inspection information 126 in relation to the structure 130. For example, if the structure 130 is a solid cube formed from a plurality of layers, the LPS 140 may detect one of the plurality of layers and provide inspection information 126 in a relation to the structure 130, such as by giving a distance between an outside layer and the detected layer.

The CAD data 150 that corresponds to the quantity of inspection information 126 may be stored on a database 170. The database 170 may be place for the storage of information or any integrated collection of logically related information that provides data for one or multiple uses. The database 170 may be a remotely accessible database, such as a database in communication over a wireless network, or a locally accessible database, such as a database that is hard-wired to the data correlation system 110, for example. In FIG. 2, the database 170 is depicted as a locally accessible database having a hard-wired communication connection to other components of the data correlation system 110.

The imaging system 160 is situated to produce the overlay image 162 having any number of images. The overlay image 162 may be produced from overlaying at least two of an image based from the structure 130, an image based from the inspection information 126, an image formed from the CAD data 150 or any other component, structure or image that is included with or in communication with the data correlation system 110. Additionally, the overlay image 162 may include the image based from the structure 130 disposed on top of the image based from the inspection information 126 using the CAD data 150. The term, "on top" may be considered a directional reference to a viewing angle of the overlay image 162, wherein the image on top is located between another image and a viewer of the overlay image 162. The overlay image 162 may include an image of an area of the structure 130, wherein the area has at least one precisely-defined point with an orientation.

The data correlation system 110 may also include a coordination system 180 in communication with the local positioning system 140. The coordination system 180 may be any system capable of providing a coordinate system for location reference. In other words, the coordinate system 180 may provide a reference to a point in an n-dimensional space, wherein the coordinate system 180 may include any number of dimensions, locations, scales or coordinate-identification mechanisms. For example, this may include a three-dimensional coordinate location reference such as an "(x,y,z)" coordinate system. The coordinate system 180 may include radial coordinates, linear coordinates, or any combination thereof. Within the aircraft industry, a common coordinate system 180 is the airplane coordinate system, in which the structure of an airplane is given a three-dimensional axis system to provide the coordinates of any point on the airplane structure.

The data correlation system 110 may also include a quantity of structural information 190 in communication with the scanning system 120, the imaging system 160 and the LPS 140, or any combination there of. The quantity of structural information 190 may include information that involves some aspect of the structure 130, such as technical specifications including structural measurements, structural tolerances, materials information or another related aspect. For example, the structural information 190 may be information about the composition of a material within the structure 130. As with other components of the data correlation system 110, the communication between the structural information 190 and the scanning system 120, the imaging system 160 and the LPS 140 may be a wireless connection, a hard-wired connection, an integral connection or any other communication connection. The structural information 190 may be situated to provide preliminary assessment information about at least a portion of the inspection information 126. The preliminary assessment information may be any information that a technician or engineer could use to make an assessment of an aspect of the structure 130.

Figure 3:
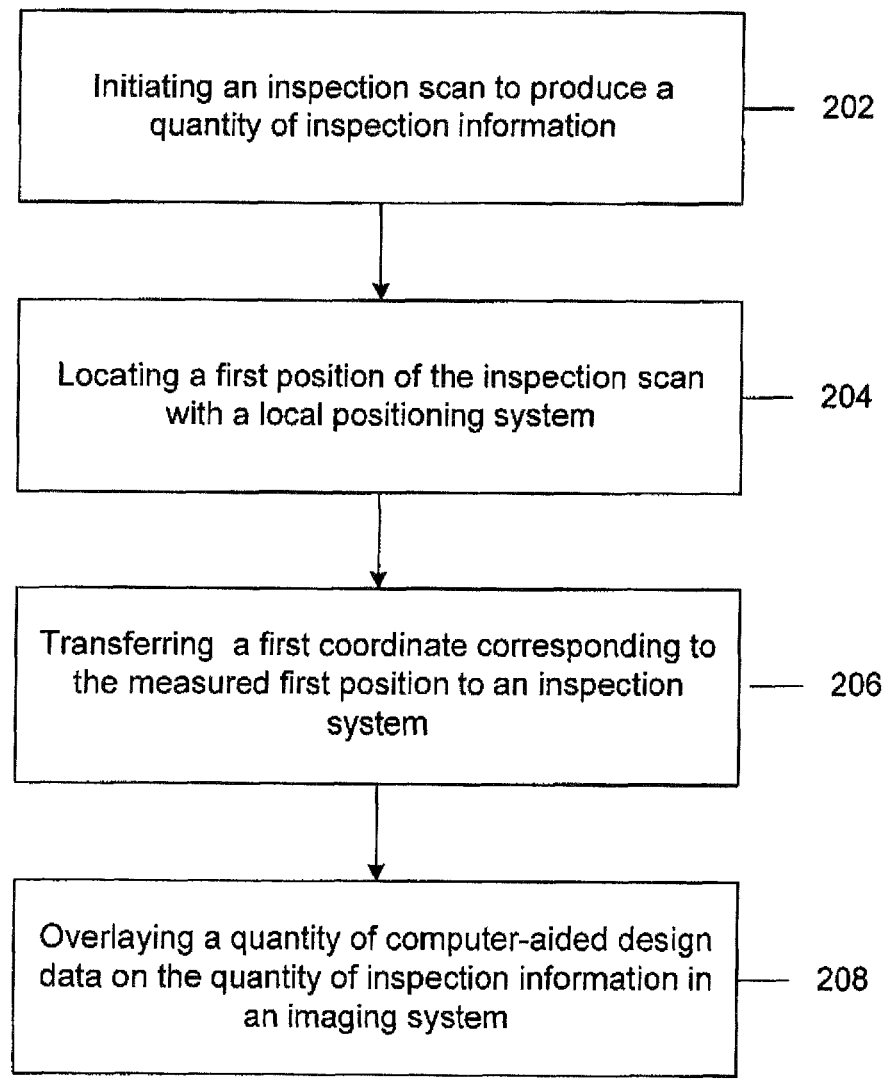
FIG. 3 is a flowchart illustrating a method of correlating data for improved structural assessment, in accordance with a third exemplary embodiment of the present disclosure.

FIG. 3 is a flowchart 200 of a method of correlating data for improved structural assessment, in accordance with a third exemplary embodiment of the present disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved.

The method of correlating data includes the step of initiating an inspection scan to produce a quantity of inspection information (Block 202). A first position of the inspection scan is located with a local positioning system (Block 204). A first coordinate corresponding to the measured first position is transferred to an inspection system (Block 206). A quantity of computer-aided design data is overlaid on the quantity of inspection information in an imaging system (Block 208).

The method of correlating data may also include the step of locating a second position or an orientation of the first position relative to the inspection information of the inspection scan. Accordingly, the step of transferring at least one of a second coordinate corresponding to the measured second position and a calculated second position based on the first position and first position scan orientation to the non-destructive inspection system may also be included. The step of overlaying a quantity of computer-aided design data on the quantity of non-destructive inspection information in the imaging system may also be included. The quantity of non-destructive inspection information may correspond to the measured second position.

Other steps may also be included in the method for correlating data. The step of determining an amount of damage to the structure may be included. The quantity of inspection information may be indicative of the amount of damage to the structure. The step of accessing structural engineering information to determine a criticality of the damage to the structure of the airplane may be included. The step of automatically accessing a repair to at least a portion of the amount of damage of the structure of the airplane may also be included. Further, the step of repairing at least a portion of the amount of damage to the structure may also be included. The inspection scan may include a non-destructive inspection scan.

Figure 4:
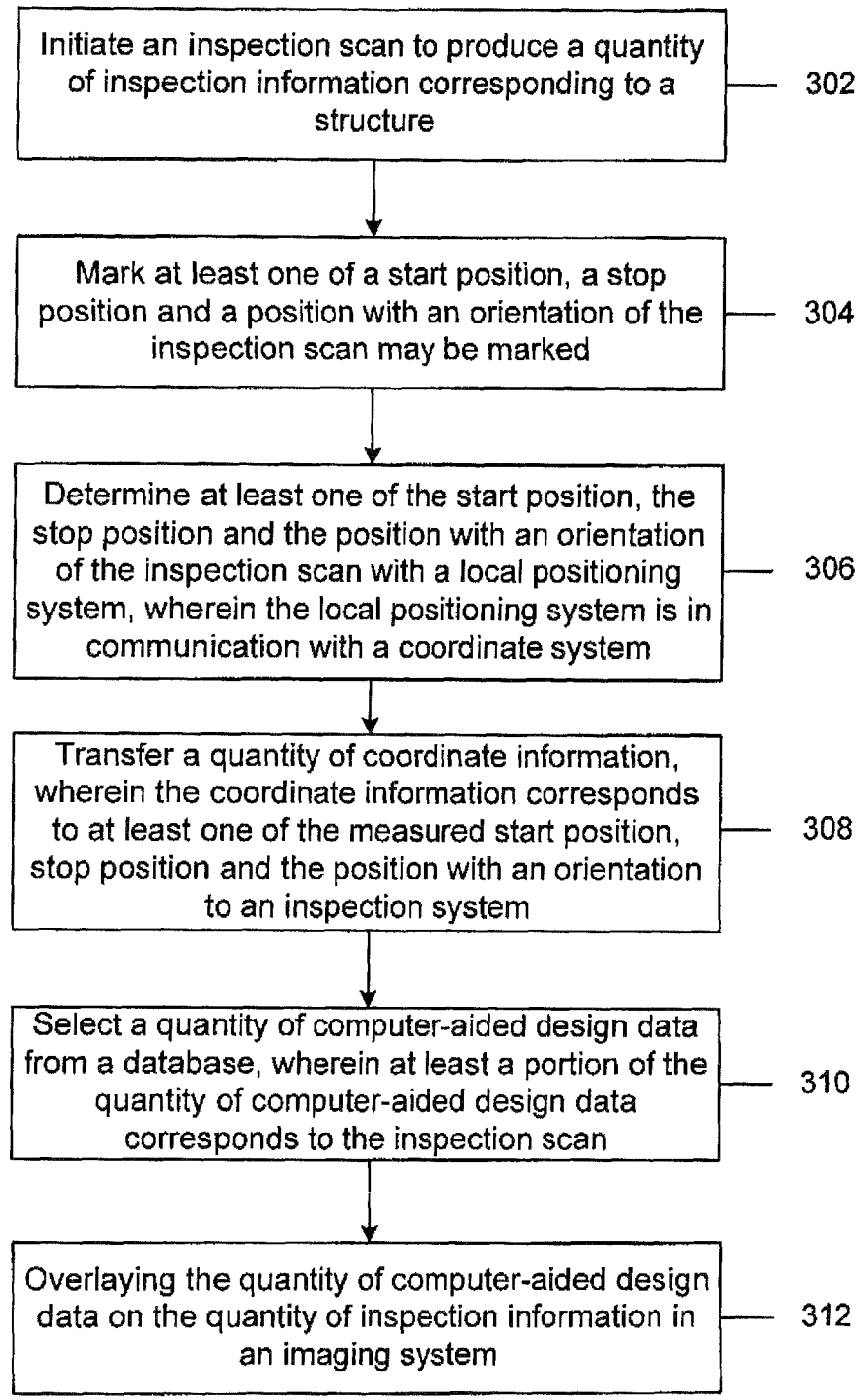
FIG. 4 is a flowchart illustrating a computer readable medium encoded with computer readable program code having operable instructions, in accordance with a fourth exemplary embodiment of the present disclosure.

FIG. 4 is a flowchart 300 illustrating a computer readable program code having operable instructions for a computer readable medium, in accordance with a fourth exemplary embodiment of the present disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved.

The program code may initiate an inspection scan to produce a quantity of inspection information corresponding to a structure (block 302). The inspection information may be non-destructive inspection (NDI) information or non-NDI information. At least one of a start position, a stop position and a position with an orientation of the inspection scan may be marked (block 304). The program code may also determine at least one of the start position, the stop position and the position with an orientation of the inspection scan with a local positioning system (block 306). The program code may determine at least one of the start position, the stop position and the position with an orientation through any method of making a determination, including, but not limited to calculating and measuring. The local positioning system may be in communication with a coordinate system. A quantity of coordinate information may be transferred (block 308). The coordinate information may correspond to at least one of the measured start position, stop position and the position with an orientation to an inspection system. The program code may select a quantity of computer-aided design data from at database may be included (block 310). At least a portion of the quantity of computer-aided design data may correspond to the inspection scan. The program code may overlay the quantity of computer-aided design data on the quantity of inspection information in an imaging system (block 312).

The structure within the operable instructions 300 may include any structure, including those referred to in any of the first through third embodiments. One common structure may be an aircraft vessel, such as a jet, an airplane or a helicopter. The database included in the operable instructions 300 may be a remote database and a local database, or a combination thereof. The operable instructions 300 of the program code may also include an instruction to retrievably store at least one of the quantity of inspection information, the measured start position and stop position, the quantity of coordinate information and the quantity of computer-aided design data.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

What is claimed is:

1. A data correlation system comprising:
 a scanning system having at least one inspection emitter, the scanning system situated to scan a portion of a structure and produce a quantity of inspection information;

a local positioning system in communication with the scanning system and situated to detect a location of the portion of the structure in relation to the structure;

a quantity of computer-aided design data corresponding to the quantity of inspection information; and an imaging system in communication with the scanning system and the local positioning system, the imaging system situated to produce an overlay image from at least two of:

an image based from the portion of the structure;

an image based from the quantity of inspection information; and an image formed from at least a portion of the quantity of computer-aided design data, wherein the imaging system situated to produce the overlay image further comprises an additional overlay image of the structure on top of the image based from the quantity of inspection information using the quantity of computer-aided design data.

2. The data correlation system of claim 1, further comprising a coordination system in communication with the local positioning system.

3. The data correlation system of claim 1, further comprising a quantity of structural information, communicated to the scanning system, the imaging system and the local positioning system, wherein the quantity of structural information is situated to provide preliminary assessment information about at least a portion of the quantity of inspection information.

4. The data correlation system of claim 1, wherein the local positioning system is situated to detect the location of the portion of the structure in relation to the structure within a 2% degree of accuracy.

5. The data correlation system of claim 1, wherein the scanning system is an ultrasonic-based scanning system.

6. The data correlation system of claim 1, wherein the scanning system is a non-destructive inspection system.

7. The data correlation system of claim 1, wherein the quantity of inspection information includes at least one of a scan start position, a scan stop position and a scan position with an orientation.

8. The data correlation system of claim 1, wherein at least a portion of the quantity of inspection information produced by the scanning system corresponds to a scan starting point with an orientation.

9. The data correlation system of claim 1, wherein the quantity of computer-aided design data corresponding to the quantity of inspection information is stored on a database, wherein the database is at least one of a remotely accessible database and a locally accessible database.

10. The data correlation system of claim 1, wherein the overlay image includes an image of a portion of the structure, wherein the portion has at least one precisely-defined point with an orientation.

11. A method of correlating data for improved structural assessment, the method comprising:

initiating an inspection scan to produce a quantity of inspection information;

locating a first position of the inspection scan with a local positioning system;

transferring a first coordinate corresponding to the measured first position to an inspection system;

overlaying a quantity of computer-aided design data on the quantity of inspection information in an imaging system locating a second position or an orientation of the first position relative to the inspection information of the inspection scan;

transferring at least one of a second coordinate corresponding to the measured second position and a calculated second position based on the first position and first position scan orientation to the non-destructive inspection system; and overlaying a quantity of computer-aided design data on the quantity of inspection information in the imaging system, wherein the quantity of inspection information corresponds to the measured second position.

12. The method of correlating data for improved structural assessment of claim 11, further comprising the step of determining an amount of damage to the structure, wherein the quantity of inspection information is indicative of the amount of damage to the structure.

13. The method of correlating data for improved structural assessment of claim 12, further comprising the step of automatically accessing a repair to at least a portion of the amount of damage of the structure of the airplane.

14. The method of correlating data for improved structural assessment of claim 12, further comprising the step of repairing at least a portion of the amount of damage to the structure.

15. The method of correlating data for improved structural assessment of claim 11, further comprising the step of accessing structural engineering information to determine a criticality of the damage to the structure of the airplane.

16. The method of correlating data for improved structural assessment of claim 11, wherein the inspection scan further comprises a non-destructive inspection scan.

17. A non-transitory computer readable medium encoded with computer readable program code, the computer readable program code comprising instructions operable to:

initiate an inspection scan to produce a quantity of non-destructive inspection information corresponding to a structure;

mark at least one of a start position, a stop position and a position with an orientation of the inspection scan;

determine at least one of the start position, the stop position and the position with an orientation of the inspection scan with a local positioning system, wherein the local positioning system is in communication with a coordinate system;

transfer a quantity of coordinate information, wherein the coordinate information corresponds to at least one of the determined start position, stop position and position with an orientation to an inspection system;

select a quantity of computer-aided design data from at database, wherein at least a portion of the quantity of computer-aided design data corresponds to the inspection scan; and overlay the quantity of computer-aided design data on the quantity of non-destructive inspection information in an imaging system.

18. The non-transitory computer readable medium of claim 17, wherein the program code further comprises instructions operable to retrievably store at least one of the quantity of non-destructive inspection information, the measured start position and stop position, the quantity of coordinate information and the quantity of computer-aided design data.

* * * * *